J. C. Hempel.

Diaper.

4424

Reissued Jun 13 1871

Witnesses.
C. H. Poole
John R. Young

Inventor.
John C. Hempel,
by Prindle & Byers,
Attys.

UNITED STATES PATENT OFFICE.

JOHN C. HEMPEL, OF BALTIMORE, MARYLAND.

IMPROVEMENT IN DIAPERS.

Specification forming part of Letters Patent No. 91,334, dated June 15, 1869; reissue No. 4,424, dated June 13, 1871.

*To whom it may concern:*

Be it known that I, JOHN C. HEMPEL, of the city of Baltimore, in the county of Baltimore and State of Maryland, have invented certain Improvements in Diapers, of which the following is a full, clear, and exact description, reference being had to the accompanying drawing making a part of this specification, in which—

Figure 1:
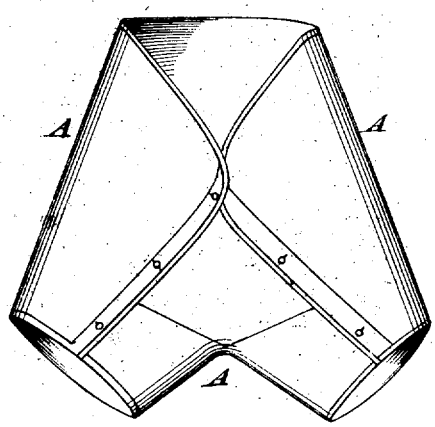
Figure 2:
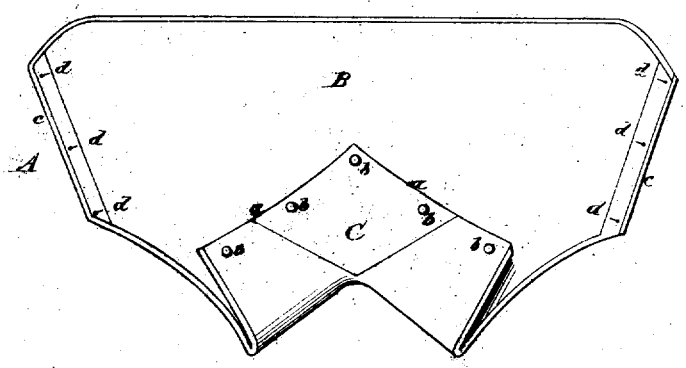

Figure 1 is a view of my diaper as it appears in use after being folded and with its proper edges secured together, and Fig. 2 a view of the same with the front turned up and with the sides not folded together.

Like letters of reference designate corresponding parts in each figure.

The object of my invention is the construction of a water-proof diaper, intended principally for the use of infants and small children, but capable of use for invalid adults, which diaper shall prevent the wetting and soiling of bed-clothing, the clothing of the wearer, and the dresses of attendants, which shall be easy and comfortable in its fit, readily removed or replaced, durable in wear, and cheap in first cost; and the invention consists in the peculiar construction of the diaper so that it may accomplish the above-named purposes, as is more fully hereinafter described and set forth.

A in the drawing represents the diaper as a whole, composed of two pieces, B and C, and made out of suitable water-proof fabric. The form and shape of these pieces, shown in Fig. 2, will insure an easy and convenient fit; but the number of pieces is not essential, or the form of the separate pieces, provided that all of the pieces when joined together have the exterior form of the diaper shown in the drawing, which form is the essential feature of my invention. The bottoms *a* of the diaper are provided with buttons *b*, and the side edges *c* with corresponding button-holes *d*, and the article is placed upon the body behind, the part C being drawn forward between the legs, and buttoned to the side edges *c*, which are brought forward and folded around the body. The diaper will then assume the pantaloon form shown in Fig. 1, and will fit easily upon the person of the wearer, and can be readily taken off or replaced.

Instead of buttons, buckles, strings, or other suitable fastening may be used.

Having thus described the purpose and manner of using my device, what I claim as new therein is—

The diaper A, substantially as described and shown.

JOHN C. HEMPEL.

Witnesses:

CHS. CRONHARD,

ALLEN E. FORRESTER.